United States Patent [19]

Bollen et al.

[11] Patent Number: 5,059,528

[45] Date of Patent: Oct. 22, 1991

[54] EXPRESSION OF HUMAN PROAPOLIPOPROTEIN A-I

[75] Inventors: Alex Bollen, Itterbeek; Jean Gobert; Ernst Wülfert, both of Brussels, all of Belgium

[73] Assignee: UCB, S.A., Brussels, Belgium

[21] Appl. No.: 198,830

[22] Filed: May 26, 1988

[30] Foreign Application Priority Data

May 28, 1987 [GB] United Kingdom ............... 8712540

[51] Int. Cl.$^5$ .................. C12P 21/06; C12N 15/00; C07H 15/12
[52] U.S. Cl. .................. 435/69.4; 435/69.1; 435/320.1; 435/255; 435/256; 435/252.3; 435/240.2; 536/27; 935/11; 935/13; 935/44; 935/45; 935/39
[58] Field of Search .................. 435/91, 172.3, 69.1, 435/69.4, 320.1, 252.33, 255, 256; 935/13, 11, 44, 45, 39; 536/27

[56] References Cited

PUBLICATIONS

Wood et al. *Nucl. Acids Res.*, vol. 12 (9) pp. 3937-3950, 1984, "The influence of messenger RNA secondary structure on expression of an immunoglobulin heavy chain in *Escherichia coli*".
Cabezon et al., *Proc. Natl. Acad. Sci.*, vol. 81(21), pp. 6594-6598, 1984, "Expression of human α 1-antitrypsin cDNA in the yeast *Saccharomyces cerevisiae*".
Lorenzetti et al., *FEBS Lett.*, vol. 194(2), pp. 343-346, 1986, "Expression of the human apolipoprotein AI gene fused to the *E. coli* gene for β-galactosidase".
Mallory et al., *J. Biol. Chem.* vol. 262(9), pp. 4241-4247, 1987, "Expression and Characterization of human apolipoprotein A-I in Chinese hamster ovary cells ".
Queen et al., *J. Mol. Appl. Genet.*, vol. 2, 1983, pp. 1-10.
Ghrayeb et al., *MBO J.*, vol. 3, 1984, pp. 2437-2442.
Matsuura et al., *J. Gen. Virol.*, vol. 67, 1986, pp. 1515-1529.

*Primary Examiner*—Robin L. Teskin

[57] ABSTRACT

The present invention provides recombinant DNA sequences comprising a sequence which codes for human proapolipoprotein A-I wherein part of the natural coding sequence has been replaced by a DNA fragment coding for the same amino acids but consisting of a different nucleotide sequence such as to reduce or prevent formation of hairpins, cloning and expression vectors containing these DNA sequences, cell cultures or microorganisms transformed with these expression vectors and processes using the same for the production of proapolipoprotein A-I.

15 Claims, 10 Drawing Sheets

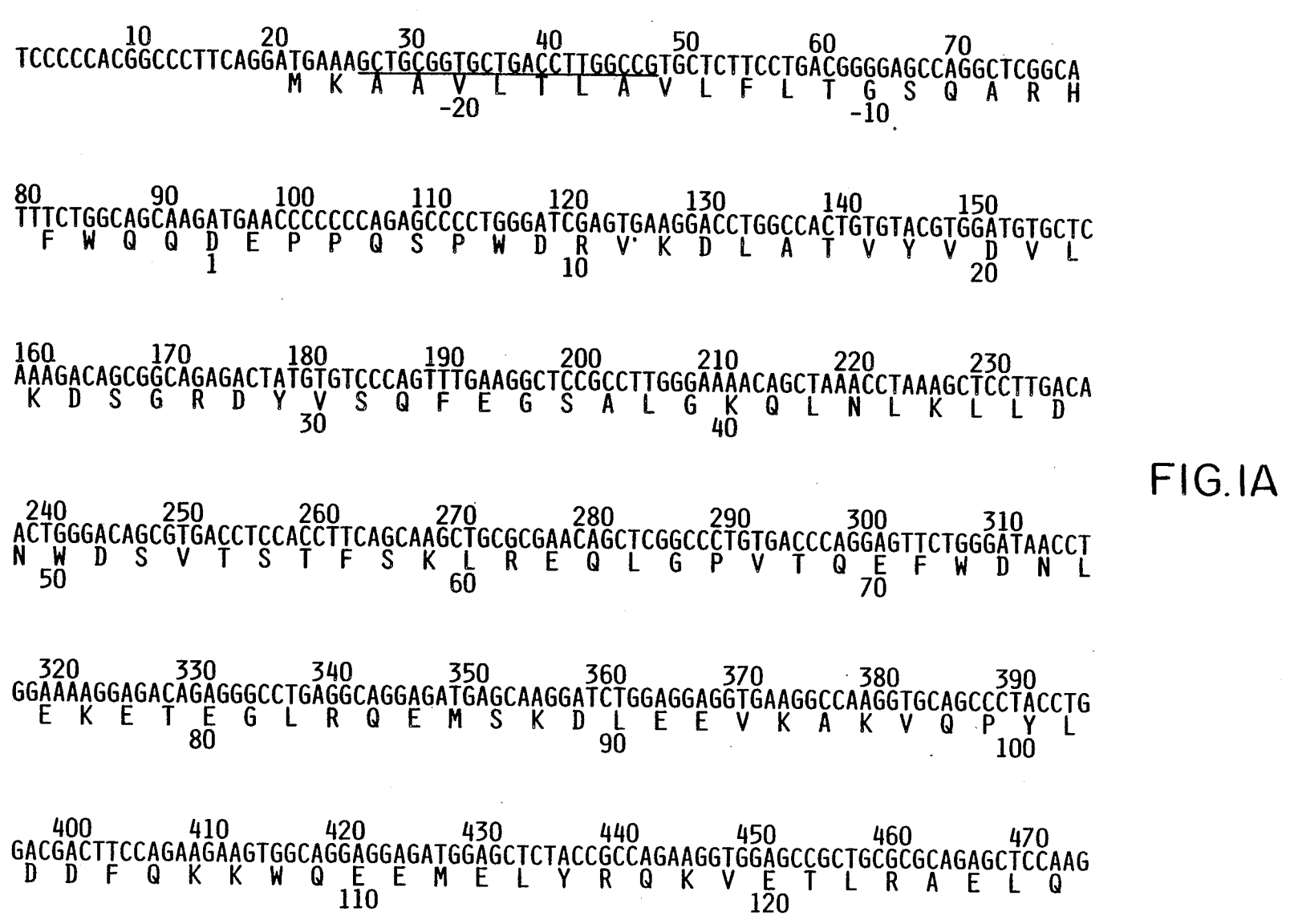

```
       480       490       500       510       520       530       540       550
AGGGCGCGCCAGAAGCTGCACGAGCTGCAAGAGAAGCTGAGCCCACTGGGCGAGGAGATGCGCGACCGCGCGGCGC
 E  G  A  R  Q  K  L  H  E  L  Q  E  K  L  S  P  L  G  E  E  M  R  D  R  A  R  A
       130                           140                           150

560       570       580       590       600       610       620       630
CCATGTGGACGGCTGCGACGAGCATCTGGCCCCCTACAGCGACGAGAGCTGCGCCAGCTGCGCCTTGGCCGCGGCTTGAGGCT
 H  V  D  A  L  R  T  H  L  A  P  Y  S  D  E  L  R  Q  R  L  A  A  R  L  E  A
              160                           170                           180

640       650       660       670       680       690       700       710
CTCAAGGAGAACGGGGGCGCCAGACTGGCCGAGTACCACGCCAAGGCCGAGTACATCTGAGCACGCTCAGCGAGAAGG
 L  K  E  N  G  G  A  R  L  A  E  Y  H  A  K  A  T  E  H  L  S  T  L  S  E  K
              190                           200

720       730       740       750       760       770       780
CCAAGCCCGCTCGAGGACCTCCGCCAAGGGCCTGCTGCCCGTGCTGGAGAGCTTCAAGGTCAGCTTCCTGAGCGCT
 A  K  P  A  L  E  D  L  R  Q  G  L  L  P  V  L  E  S  F  K  V  S  F  L  S  A
  210                           220                           230

790       800       810       820       830       840       850       860
CTCGAGGAGTACACTAAGAAGCTCAACACCCAGTGAGGGCGCCCGCCGCGCCCCCTTCCCGGTGCTCAGAATAAACGT
 L  E  E  Y  T  K  K  L  N  T  Q  Stop
                    240

870       878
TTCCAAAGTGGG
```

EXPRESSION OF HUMAN PROAPOLIPOPROTEIN A-I

FIELD OF THE INVENTION

The present invention relates to new recombinant DNA sequences comprising a sequence coding for human proapolipoprotein A-I, to cloning and expression vectors containing these DNA sequences, to host cells transformed with these expression vectors and to processes for producing human proapolipoprotein A-I by using the new recombinant DNA sequences, vectors and transformants.

BACKGROUND INFORMATION

Human apolipoprotein A-I (apo A-I) is the major protein constituent of high density lipoproteins (HDL) and lymph chylomicrons. The liver and small intestine are the primary sites of synthesis of apo A-I. In these organs, apo A-I is synthesized as a precursor protein (preproapo A-I). Cotranslational cleavage of the prepeptide occurs intracellularly and proapo A-I is secreted into the plasma and lymph.

Proapo A-I has six additional amino acids (Arg-His-Phe-Trp-Gln-Gln) attached at the amino terminal end of apo A-I. Upon reaching the vascular space, proapo A-I is cleaved, in vivo, by a specific proteolytic enzyme (apo A-I propeptidase) to yield mature apo A-I.

Mature apo A-I is a single unglycosylated polypeptide of known sequence composed of 243 amino acid residues (H. B. BREWER et al., Biochem. Biophys. Res. Commun. 80, (1978), 623-630); it serves as a cofactor for the plasma enzyme lecithin: cholesterol acyltransferase, which is responsible for the formation of most cholesterol esters in plasma. Defects in apolipoprotein structures or biosynthesis may result in disorders of the plasma lipid transport system and in the development of coronary artery disease. Low levels of apo A-I and HDL in plasma has been shown to be a strong risk factor for heart attacks (myocardial infarction) and other atherosclerotic vascular diseases. Mutations in the gene coding for apo A-I namely have been associated with reduced HDL levels and with premature coronary artery diseases.

Apo A-I and HDL are the major plasma components that participate in the transport of cholesterol from peripheral tissues (arteries) to the liver (so called reverse cholesterol transport) for excretion from the body. Since accumulation of cholesterol in the arteries is the hall-mark and most important process of atherosclerosis, stimulation of reverse cholesterol transport by supplying apo A-I may retard and reverse the atherosclerotic process and hence diminish the incidence of heart attacks.

Maturation of proapo A-I into apo A-I can occur quantitatively and extracellularly with a residence time in the blood of less than 12 hours. Since proapo A-I is the major, if not the sole, precursor to the mature apo A-I, it could be used in replacement therapy whenever HDL levels decrease, for instance in hereditary or acquired deficiencies. Because of the therapeutic utility of apo A-I in general, researchers have been looking for techniques to produce apo A-I in large quantities. Conventionnaly, such techniques have involved purification of apo A-I from blood plasma. Several publications (P. CHEUNG and L. CHAN, Nucleic Acids Res. 11, (1983), 3703-3715; J. J. SEILHAMER et al., DNA, 3, (1984), 309-317 and Japanese patent application No. 96998/86) have shown that the complementary DNA coding for preproapo A-I can be obtained by well-known genetic engineering techniques. R. LORENZETTI et al., (FEBS Lett. 194, (1986), 343-346) have shown that apo A-I can be expressed in E. coli as an uncleavable fused protein with β-galactosidase. Attempts to express mature apo A-I as an unfused protein were unsuccessful, however.

In the above-mentioned Japanese patent application No. 96998/86, there is described the expression of a human apoliprotein A-I-like protein in E. coli, which have been transformed with a plasmid pHAIE-I containing the structural apo A-I gene under control of the tac promoter. The structural gene is not complete, however, and consists of the condons for amino acids +4 to +243, preceded by an ATG translation initiation codon. As a consequence, the expression product obtained contains N-terminal methionine (corresponding to the ATG codon) which might cause secondary effects when used in therapy. J. B. MALLORY et al. (J. Biol. Chem. 262, (1987), 4241-4247; PCT International patent applications WO 86/04920 and WO 87/02062) disclose expression of human apolipoprotein A-I in Chinese hamster ovary cells (animal cell culture). The construct used contains the entire human preproapolipoprotein A-I gene. The Chinese hamster ovary cells seem to process the proapo form to the mature apo form, since only 5-10% of the secreted apo A-I protein is proapo A-I, the remainder being the mature apo A-I protein. The productivity of the system is relatively low, since $0{,}55 \times 10^6$ cells secrete only 25-30 μg/ml of apo A-I in a 24-hour period. In the PCT International patent application WO 87/02062, some examples are concerned with expression of human apolipoprotein A-I in other hosts, such as E. coli (bacterial host) and S. cerevisiae (yeast). None of the constructs used contains the genetic information for the proapo form, however, and the resulting protein is not human proapolipoprotein A-I.

SUMMARY OF THE INVENTION

The present invention is directed to the means and methods of producing human proapolipoprotein A-I via recombinant DNA technology, i.e. mature proapo A-I protein which is susceptible to cleavage by the specific proteolytic apo A-I propeptidase enzyme. The term "mature" as used herein connotes human proapo A-I as such, but also includes the corresponding protein preceded by methionine as a first amino acid which is present by virtue of the ATG translation initiation codon in the expression vector construction thereof. The present invention relates to the construction of cloning and expression vectors comprising a DNA sequence encoding human proapo A-I, such as to enable the amplification and hence, expression of the mature human proapo A-I protein, as well as Met-, fused, or signal N-terminal conjugates thereof. Likewise, the present invention relates to viable cell cultures or microorganisms genetically altered by virtue of their harboring such vectors and capable of producing human proapo A-I polypeptide. Further, the present invention provides human proapo A-I in physical state distinct from its existence in, or isolation from, a natural environment or source; by virtue of its method of preparation herein, the human proapo A-I is essentially free of usual endogenous proteins and other native materials or substances. The present invention is directed to the recombinant DNA production of human proapo A-I in all of its aspects, and is not to be construed as limited to any specific details described herein and embraced within the scope of this invention.

One basic aspect of the present invention is the production of a protein which consists of or contains mature human proapo A-I, and hence, can be converted in vitro and in vivo, into mature human apo A-I by means of the proteolytic action of apo A-I propeptidase. For therapeutical purposes, the human proapo A-I product may be used as such, including Met-proapo A-I if the presence of the methionyl residue appears to be pharmaceutically acceptable, because said product can be converted naturally and efficiently in the blood stream by the naturally occuring propeptidase to yield authentic mature human apo A-I. If desired, the human proapo A-I product may be produced in selected microorganisms or cell cultures which are able to process the N-terminal methionine, and hence, produce the human proapo A-I product in a form lacking the amino terminal methionine. Alternatively, the human proapo A-I product, regardless whether it contains or lacks an amino terminal methionine residue, may be cleaved in vitro to obtain mature human apo A-I, which can be used for therapeutical purposes. The same applies to fusion and signal N-terminus conjugates of proapo A-I: cleavage results in authentic human apo A-I which is devoid of the N-terminal methionine.

A second important aspect of the present invention is the use of a modified coding sequence for at least part of the human proapo A-I molecule, said modified coding sequence improving the translational efficiency by virtue of reduced or even prevented hairpin formation. It is possible that R. LORENZETTI et al. (FEBS Lett. 194, (1986), 343-346) were not able to detect expression of unfused mature apo A-I protein because their DNA constructs were susceptible to appreciable formation of hairpin structures resulting in very inefficient expression. Surprisingly, we have found that efficient expression can be secured by proper modification of a few codons in the coding sequence of amino acids −6 to +14 of human proapo A-I. The words "proper modification" as used herein imply that some of the natural codons are replaced by alternative codons, i.e. codons which according to the genetic code represent the same amino acids, and further imply that the modifications taken together result in a reduction or even prevention of hairpin formation. It is important to note that the modifications of the DNA sequence have no effect on the nature of the propeptidase cleavage site since the amino acid sequence recognized by the propeptidase is preserved in the construction.

On the protein level, the present invention relates to human proapo A-I as a product of a genetically altered cell culture or microorganism. Said human proapo A-I may be in the form of mature proapo A-I, in the form of mature proapo A-I preceded by a methionine residue, in the form of a fused protein such as, for example, a fused β-galactosidase-proapo A-I protein, and in the form of the preproapo A-I product. The product will be essentially free of usual endogenous proteins and other native materials or substances common to the natural source (blood plasma) of the protein concerned. The cell culture or microorganism used in the production is not limited to specific cell lines and organisms: both prokaryotic and eukaryotic cells can be utilized, including animal and human cell lines. For illustrative purposes only, we exemplify herein expression in *E. coli* bacteria (as representative of prokaryotic cells) and in the yeast *Saccharomyces cerevisiae* as well as in insect cells infected by baculovirus (as representative of eukaryotic cells). On the protein level, the present invention relates also to human apo A-I obtained by treatment of the above human proapo A-I with apo A-I propeptidase. Said human apo A-I will be identical to the authentic form of mature human apo A-I and will be devoid of any amino terminal methionine residue.

On the use level, the present invention relates to pharmaceutical compositions comprising the above human proapo A-I and/or the above human apo A-I, and further comprising at least one pharmaceutically acceptable carrier, solvent, diluent or excipient, properly selected in accordance with the route of administration and conventional considerations in the formulation of pharmaceutical compositions.

On the DNA level, the present invention relates to a recombinant DNA sequence comprising a sequence which codes for human proapo A-I, wherein part of the natural coding sequence has been replaced by a DNA fragment coding for the same amino acids but consisting of a different nucleotide sequence such as to reduce or prevent formation of hairpins. In a specific preferred embodiment, the natural sequence coding for the amino acids −6 to +14 of proapo A-I has been replaced by the sequence (only one strand shown):

5'-ATGAGACATTTCTGGCAGCAGGAC-
GAACCTCCACAATCTCCTTG-
GGATAGAGTTAAGGACTTG-3' said sequence comprising an added ATG translation initiation codon and modified codons for the amino acid residues −6, −1, +1, +3, +4, +5, +6, +7, +10, +11 and +14.

On the DNA level, the present invention also relates to replicable cloning vectors and expression vectors comprising the aforesaid recombinant DNA sequence which codes for human proapo A-I. The present invention specifically relates to the recombinant plasmids pULB9291, pULB9292, pULB9296, pULB9299, pNIV1612 and pNIV1613, the construction of which is described hereinafter. The first mentioned plasmids pULB9291 and pULB9292 contain the modified proapo A-I structural gene preceded by an ATG codon and under control of the phage lambda $P_L$ promoter. The plasmids are suitable expression vectors for *E. coli* and direct the synthesis of human proapo A-I which can be cleaved by the propeptidase to generate authentic mature human apo A-I. The plasmid pULB9296, when introduced in *E. coli*, directs the expression of a fused protein comprising β-galactosidase and human proapo A-I under control of the *E. coli lac* promoter region. Since the fused product still contains the propeptidase cleavage sequence, it can be cleaved to yield authentic mature human apo A-I.

The plasmid pULB9299 is a suitable expression vector for yeast species and comprises the ARG3 promoter and transcription terminator regions to secure efficient expression in yeast. Again, the human proapo A-I product can be cleaved by the propeptidase to yield authentic mature human apo A-I. The plasmid pNIV1612 contains the proapo A-I structural gene fused to the DNA sequence of the *E. coli* ompA protein signal peptide and under control of the lpp (lipoprotein) promoter and of the lac promoter-operator. In the construction, the sequence coding for the ompA signal peptide precedes the proapo A-I sequence without the ATG translation initiation codon. The plasmid is a suitable secretion vector for *E. coli* and directs the synthesis of human proapo A-I which can be secreted in the periplasm without N-terminal methionine. The plasmid pNIV1613 is a transfer vector for the introduction of human proapo A-I cDNA sequence into baculovirus. It comprises the polyhedrin promoter of the baculovirus and the proapo A-I structural gene, including the ATG translation initiation codon. In conjunction with the wild type baculovirus (*Autographa californica* nuclear polyhedrosis virus, AcNPV), the plasmid pNIV1613 directs the synthesis in insect cells of proapo A-I, which can be free of methionine after post-translational modifications in insect cells.

Finally, the present invention also relates to cell cultures and microorganisms which have been transformed with a cloning vector or an expression vector as described above, in particular transformed cell cultures and microorganisms which are capable of producing human proapo A-I. The term "transformed" as used herein has the broad meaning of "genetically altered" and is certainly not limited to the narrow concept of "bacterial transformation". Depending of the kind of vector used and the host selected therefor, any compatible genetic engineering technique to obtain the sought genetic alteration can be used, including transfection, transduction, etc. Cell cultures and microorganisms produced according to the invention can be used in industrial scale fermentative production of human proapolipoprotein A-I.

DESCRIPTION OF PREFERRED EMBODIMENTS

The invention described herein was performed employing, inter alia, the microorganism *E. coli* K12 strain MM 294 (endoA thi-, hsdR, supE); this strain has been deposited with the American Type Culture Collection (ATCC No. 33625) without restriction as to access. However, various other microbial strains are useful, including known *E. coli* strains such as *E. coli* B, *E. coli*×1776 (ATCC No. 31537, deposited July 3, 1979 without restriction), *E. coli* AR58 an N 99 (ATCC No. 33956) derivative with cIII−, cI 857, bio-, lambda defective delta H functions, sold by PL-PHARMACIA (J. E. MOTT et al. Proc. Natl. Acad. Sci. USA, 82, (1985) 88–92; G. DEVARE et al., Cell, 36, (1984), 43–49) *E. coli* JM101 (ATCC No. 33876) (J. MESSING et al., Nucelic Acids Res. 9, (1981) 309–321), or *E. coli* JA221 (lpp−, hdsM+, trpE5, leuB6, lacY, recAI/F', laqI$^q$, lac+, pro+) (J. GHRAYEB et al., EMBO J., 3, (1984), 2437–2442) or other microbial strains many of which are deposited and available from recognized microorganism depositary institutions, such as the American Type Culture Collection (ATCC)—cf. the ATCC catalogue listing. These other microorganisms include, for example, Bacilli such as *Bacillus subtilis* and other Enterobacteriaceae among which can be mentioned as examples *Salmonella Typhimurium* and *Serratia marcesans*, utilizing plasmids that can replicate and express heterologous gene sequences therein.

Expression plasmids for bacterial use, e.g. *E. coli*, are commonly derived using pBR322 as vector (deposited in the ATCC under accession number 37017) and appropriately inserting the heterologous gene sequence together with translational start and stop signals in operable reading frame with a functional promoter, taking advantage of common or synthetically created restriction sites. The vector will carry one or more phenotypic selection characteristic genes and an origin of replication to insure amplification within the host. Again, the heterologous insert can be aligned so as to be expressed together with a fused presequence, derivable for example from the lac system genes.

Baculovirus expression vectors, e.g. pAcRP6 or pAcYM1 (Y. MATSUURA et al., J. Gen. Virol. 68, (1987), 1233–1250) and wild type baculovirus (*Autographa californica* nuclear polyhedrosis virus, AcNPV) are now widely used. They are described in detail in the literature and can be obtained namely from the Texas Agricultural Experiment Station.

According to the present invention, there may also be used various insect cells, as host for compatible expression vectors, such as *Spodoptera frugiperda* cells, Sf9 (M. D. SUMMER and G. E. SMITH. A Manual of Methods for Baculovirus Vectors and Insect cell culture Procedures, Texas University, College Station, (1987); ATCC CRL 1711).

According to the present invention, there may also be used various yeast strains, hosting compatible expression vectors, such as the plasmid YRp7 (D. T. STINCHCOMB et al., Nature, 282, (1979), 39–43) which is capable of selection and replication in both *E. coli* and yeast, particularly *Saccharomyces cerevisiae*. Useful yeast strains are strain RH218 (G. MIOZZARI et al., J. Bacteriol. 134, (1978), 48–59) deposited with the American Type Culture Collection without restriction (ATCC No. 44076), the 10S44c strain (T. CABEZON et al., Proc. Natl. Acad. Sci. USA, 81, (1984), 6594–6598) which has the leu2-3, leu2-112, pep 4-3 genotype (M. HOYLAERTS et al., FEBS Lett. 204, (1986) 83–87) and strain Ic 1697d (argJ, leu2-1) an arginine bradotroph (ATCC No. 20631).

To express a heterologous gene such as the cDNA for human proapo A-I in yeast, it is necessary to construct a plasmid vector containing four components.

The first component is the part which allows for transformation of both *E. coli* and yeast and thus must contain a selectable gene from each organism. This can be the gene for ampicillin resistance from *E. coli* (cf. "AmpA") and the gene leu2 from yeast. This component also requires an origin of replication from both organisms to be maintained as a plasmid DNA in both organisms. This can be the *E. coli* origin from pBR322 and the arsl origin from chromosome III of yeast or the origin of replication from 2μ circle DNA. The second component of the plasmid is a 5'-flanking sequence from a highly expressed yeast gene to promote transcription of a downstream-placed structural gene. The 5'-flanking sequence can be that from the yeast TDH3 or ARG3 genes. The fragment is constructed in such a way so as to remove the TDH3 or ARG3 structural sequences, replaced with a sequence containing alternative restriction sites, such as NcoI or BamHI restriction sites, for convenient attachment of this 5'-flanking sequence to the structural gene. The third component of the system is a structural gene constructed in such a manner that it contains both an ATG translational start and translational stop signals.

The fourth component is a yeast DNA sequence containing the 3'-flanking sequence of a yeast gene, which contains the proper signals for transcription termination and polyadenylation. For example, plasmids directing the production of human proapo A-I in yeast can be constructed by inserting gene fragments for the human proapo A-I polypeptide into the BamHI site of expression plasmid pRIT10774 as described in European patent application No. 151102.

BRIEF DESCRIPTION OF THE DRAWINGS

FIGS. 1A,B show the nucleotide and amino acid sequence of human preproapo A-I. The nucleotide sequence of the human preproapo A-I mRNA was determined from DNA sequence analysis of the cDNA clone pULB1609. Predicted amino acids of the signal peptide, propeptide and mature apo A-I polypeptide are shown and are numbered from the first amino acid residue of the apo A-I protein. The region corresponding to the synthetic DNA probe used to isolate the clone is underlined.

The one-letter abbreviations for amino acid residues are: A, alanine; C, cysteine; D, aspartic acid; E, glutamic acid; F, phenylanine; G, glycine; H, histidine; I, isoleucine; K, lysine; L, leucine; M, methionine; N, asparagine; P, proline; Q, glutamine; R, arginine; S, serine; T, threonine; V, valine; W, tryptophane; and Y, tyrosine.

Figure 2:
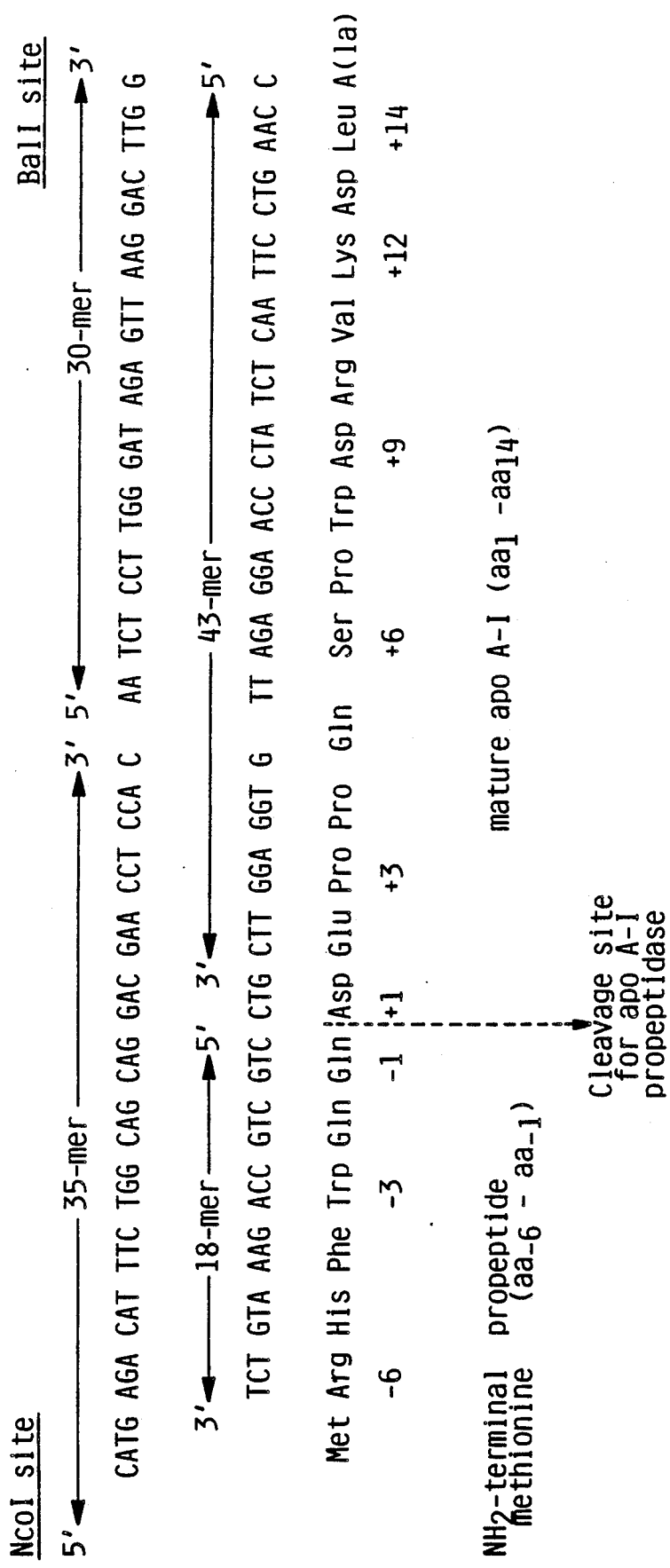

FIG. 2 depicts the synthetic scheme of an oligonucleotic adapter for the construction of a DNA fragment coding for the 6 amino acids of the propeptide and for the first 14 amino acids of mature apo A-I polypeptide, together with the start ATG codon. The arrows indicate the oligonucleotides used to synthesize the 65/61 bp NcoI-BalI fragment.

Figure 3:
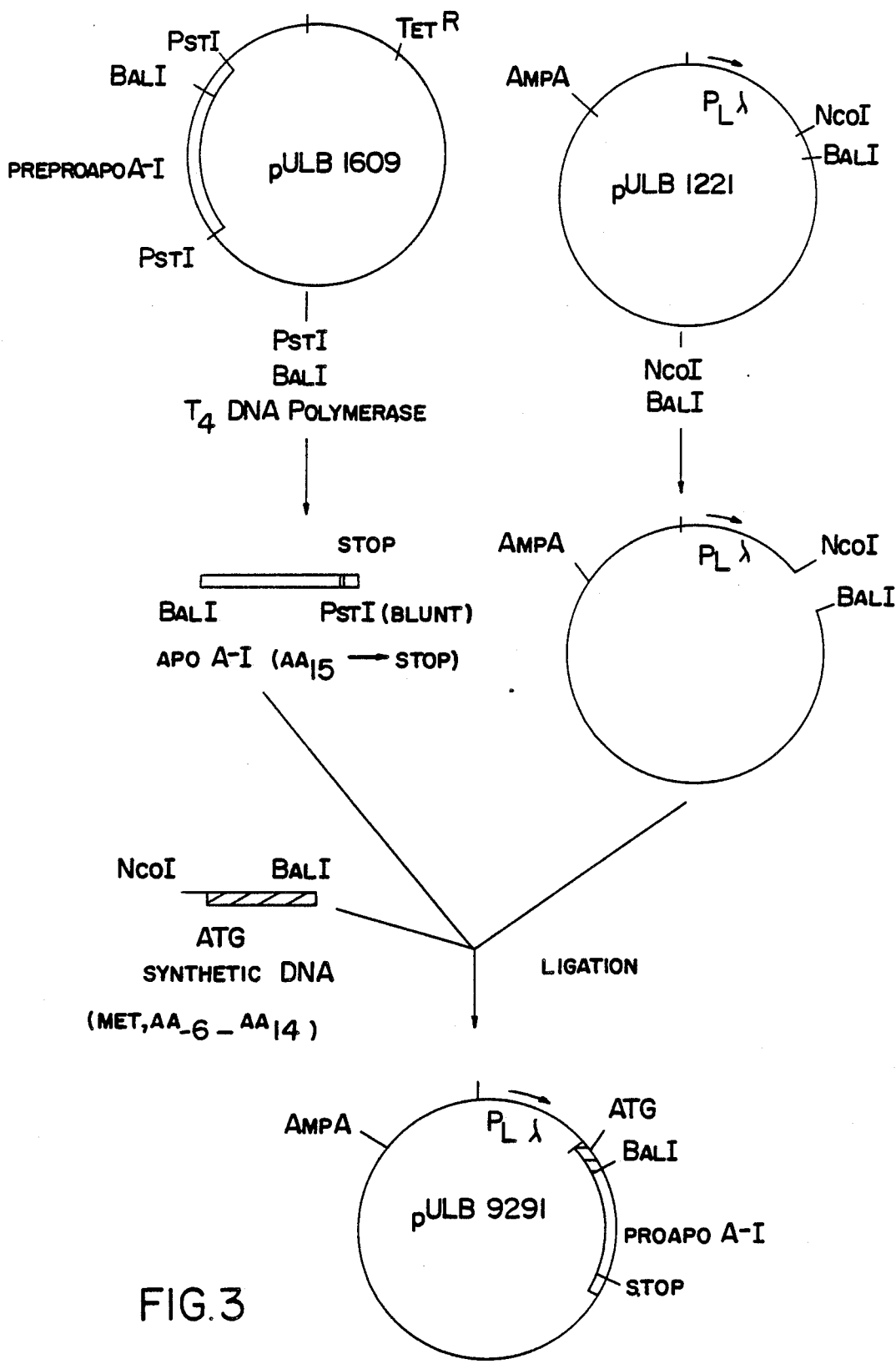

FIG. 3 shows the construction of pULB9291 which carries the $P_L$ lambda regulatory regions and the proapo A-I nucleotide sequence.

Figure 4:
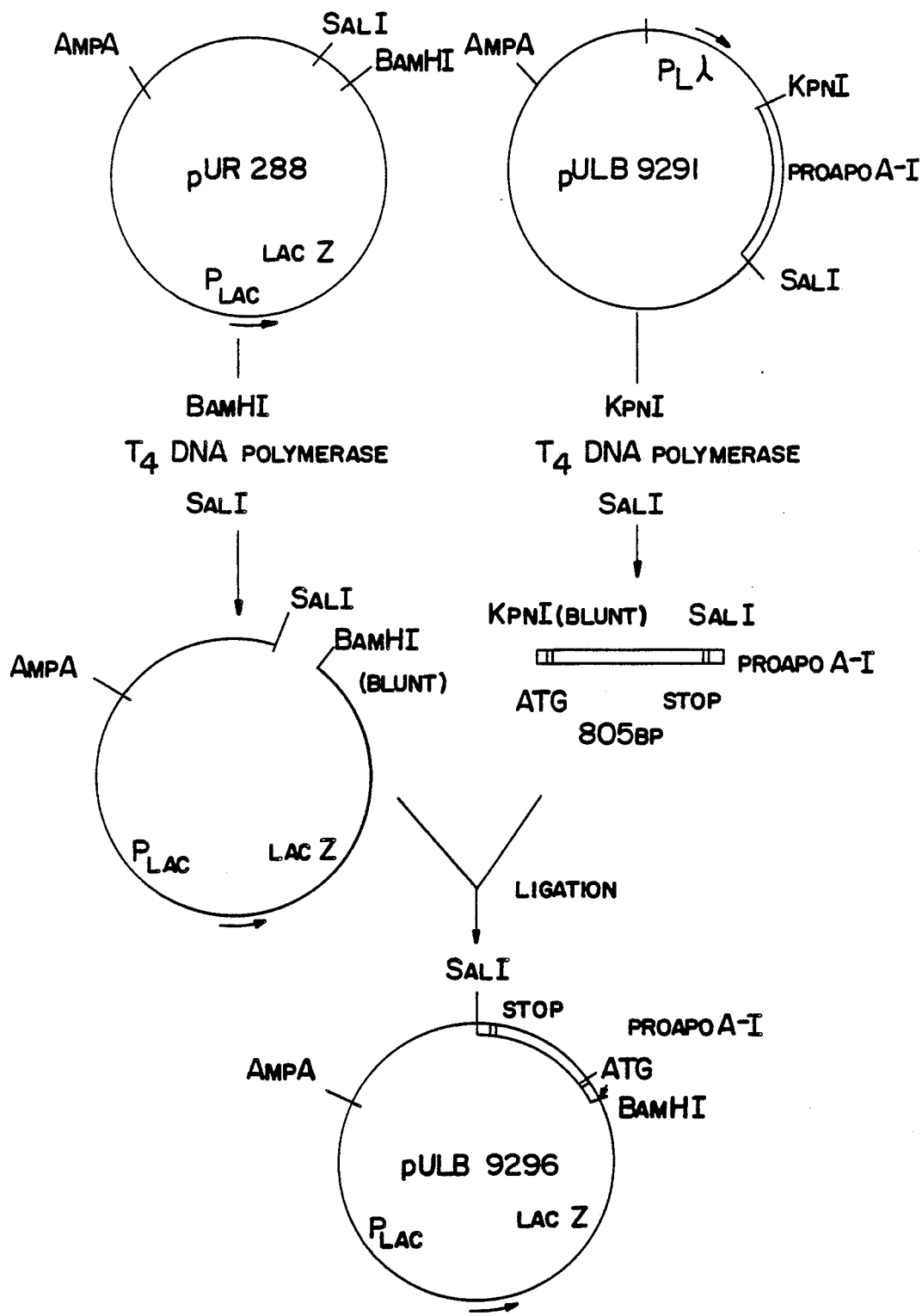

FIG. 4 shows the construction of pULB9296 which carries the *E. coli lac* promoter and a fused beta-galactosidase- proapo A-I nucleotide sequence.

Figure 5:
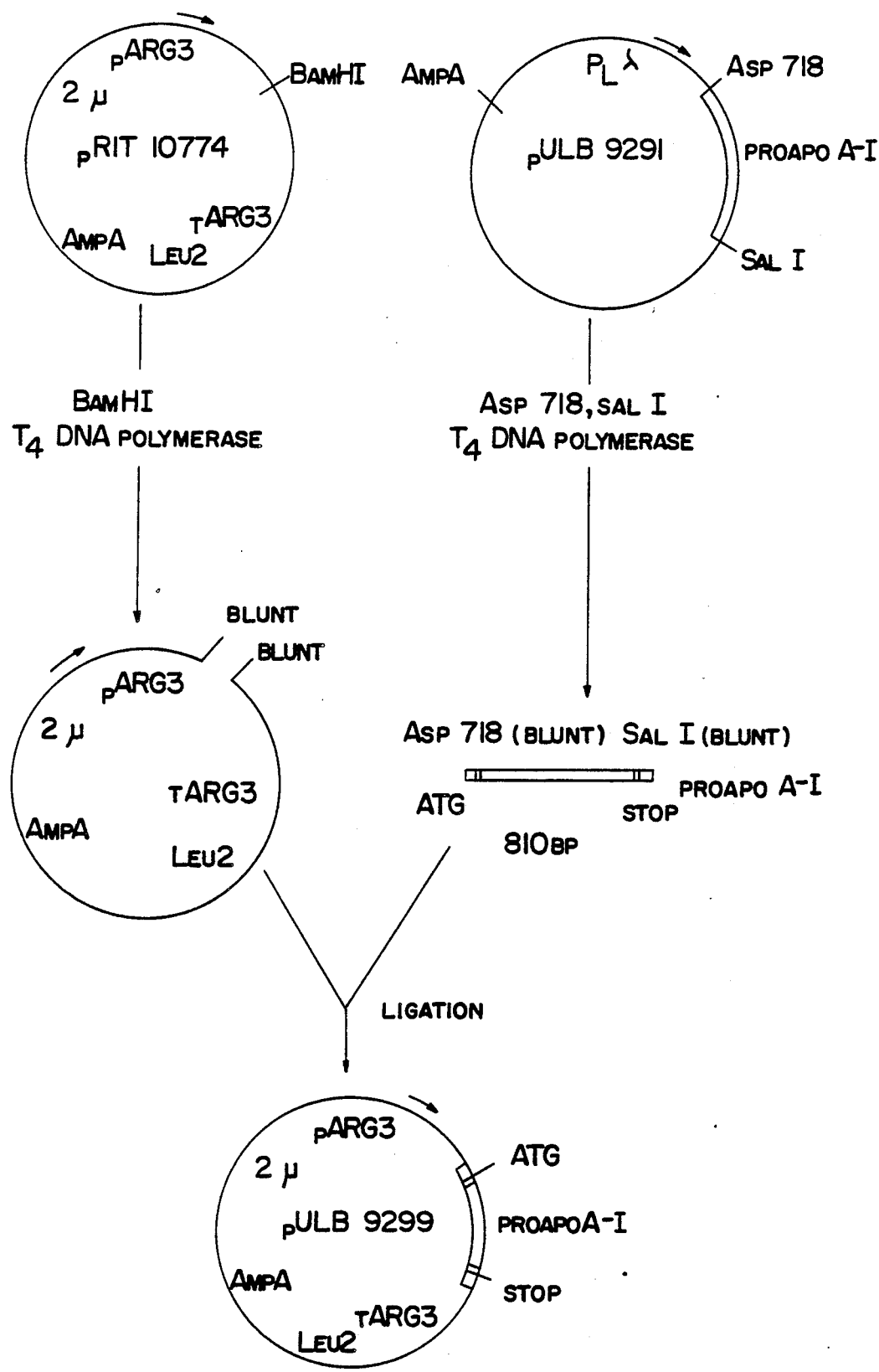

FIG. 5 shows the construction of pULB9299 which carries the yeast ARG3 regulatory regions and the proapo A-I nucleotide sequence.

Figure 6A:
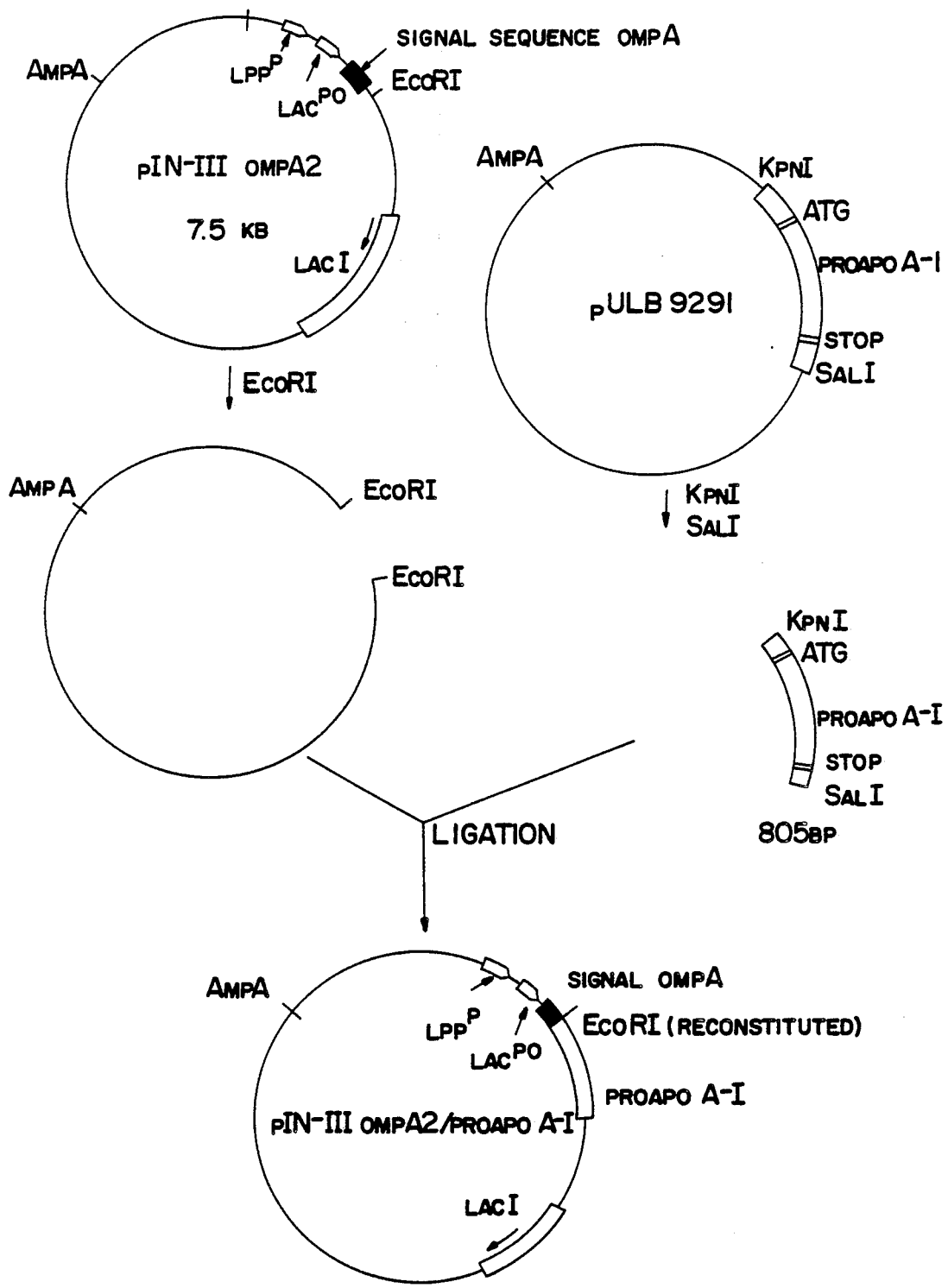
Figure 6B:
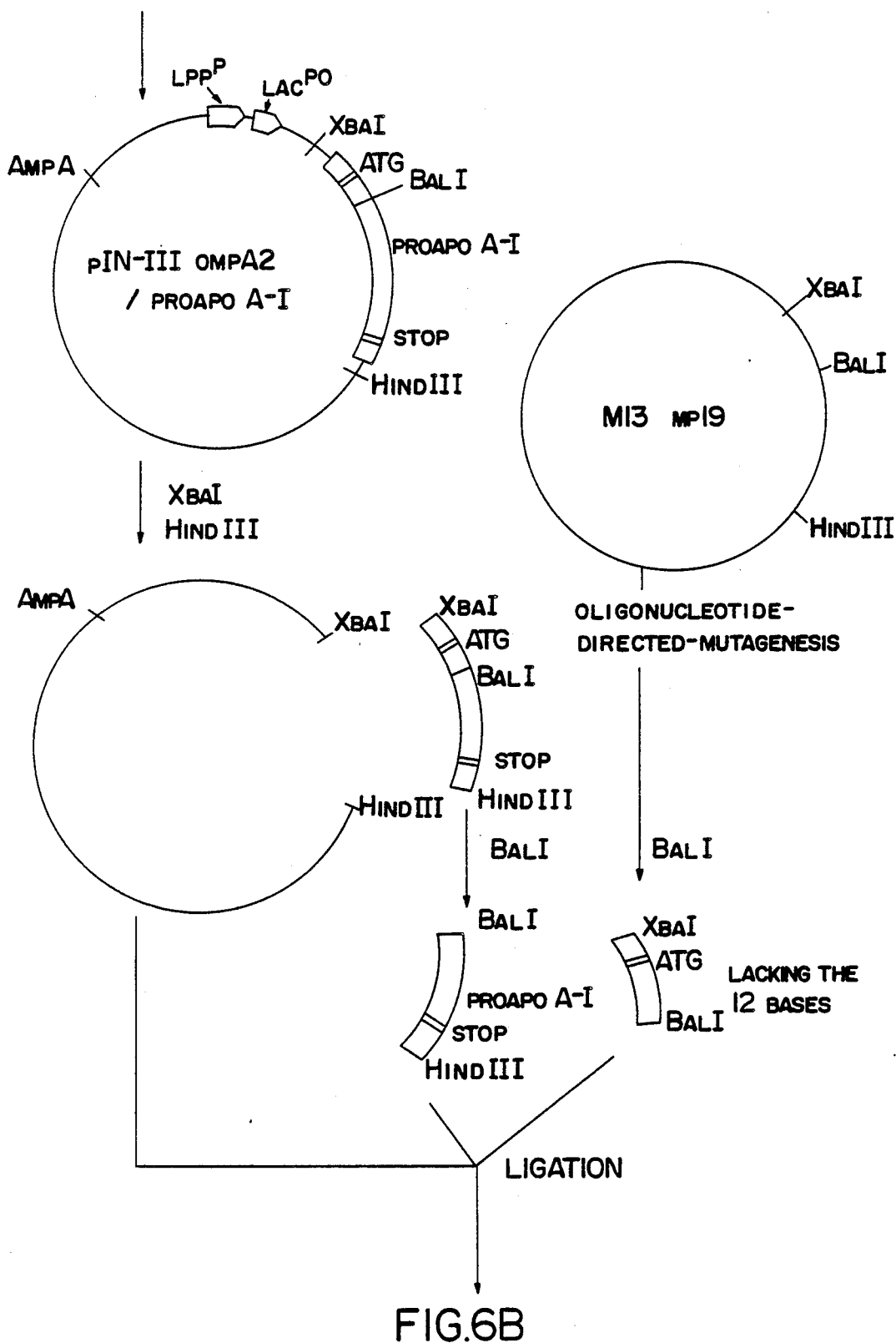
Figure 6C:
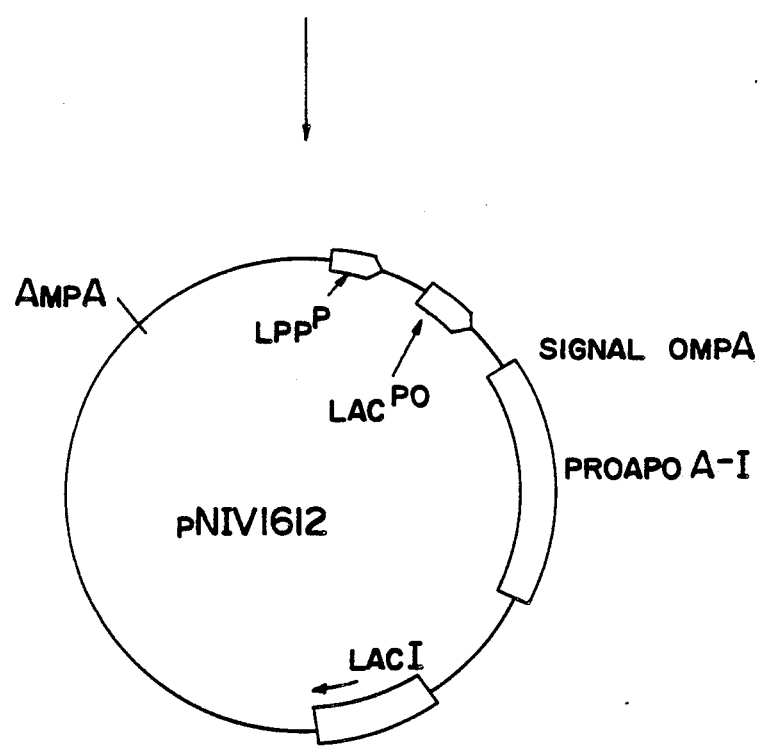

FIGS. 6A,B,C show the construction of pNIV1612 which carries the lac and the lpp regulatory regions, the sequence coding for the ompA signal peptide and the proapo A-I nucleotide sequence.

Figure 7:
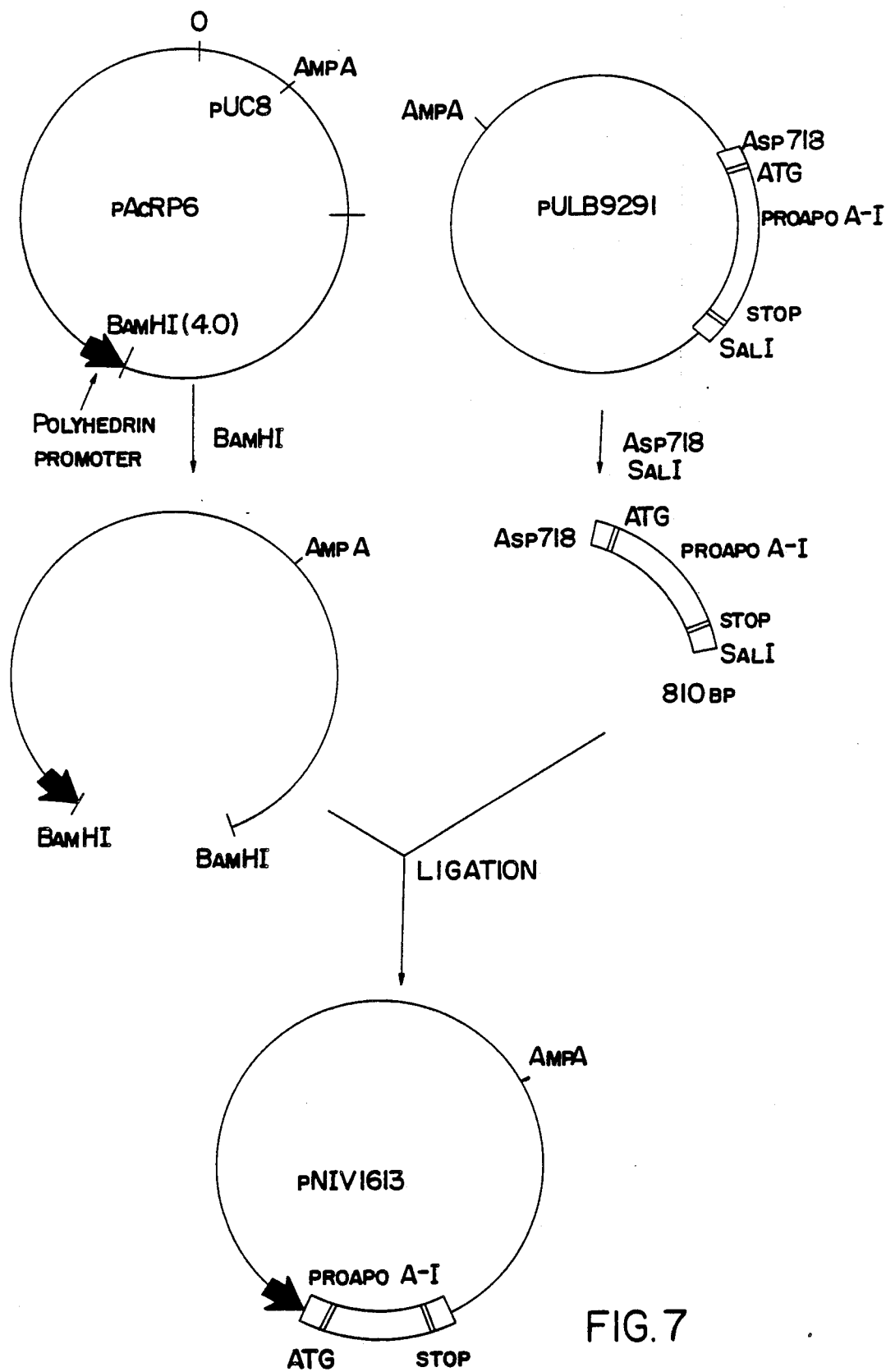

FIG. 7 shows the construction of pNIV1613 which carries the polyhedrin gene regulatory region and the proapo A-I nucleotide sequence.

DETAILED DESCRIPTION OF THE INVENTION

RNA preparation: Human liver total RNA was prepared by the guanidinium chloride method (R. A. COX, Methods Enzymol. XII, part B, (1968), 120–129). This total RNA preparation was then passed onto an oligo(dT) cellulose column to obtain the total polyA+RNAs (T. MANIATIS et al., in Molecular Cloning (Cold Spring Harbor Laboratory, Cold Spring Harbor, N.Y., 1982). 200 µg of polyA+RNAs were obtained from 10 g of human liver.

Synthesis in vitro of the complementary DNA (cDNA)

The reverse transcription reactions, containing from 0.1 to 5 µg of total polyA+RNAs, were primed with oligo(dT)$_{12-18}$ (approximatively 1 µg; source: BOEHRINGER). The single-stranded cDNA was then converted to the double-stranded molecule (cDNAds) with the same reverse transcriptase enzyme. cDNAds preparations, usually 1 µg, were treated with S1 nuclease to create blunt-ended extremities. The procedures are well-known in the art and described in detail by T. MANIATIS et al., loc. cit. cDNAds were then oligo(dC)-tailed by the technique described by L. VILLA-KOMAROFF et al., (Proc. Natl. Acad. Sci. USA, 75, (1978), 3727–3731). Usually, 100 ng of cDNAds are treated by the enzyme terminal deoxynucleotidyl transferase. In general, 15-base-long extensions are added to the 3' ends of the cDNAds molecules.

Cloning of the tailed cDNAds into the plasmid vector pBR322 pBR322 plasmid DNA was linearized by the enzyme PstI and oligo(dG)-tailed as described by R. M. LAWN et al. (Nucleic Acids Res. 9, (1981), 6103–6114). Oligo(dC)-tailed cDNAds were mixed with oligo(dG)-tailed pBR322 DNA in equimolar ratios. Usually, 50 µg of the mixture was annealed to recircularize the plasmid. Conditions are well-known in the art and are detailed by R. M. LAWN et al., loc. cit. The annealed mixture was then used to transform competent *E. coli* cells, strain MM294, as described by R. M. LAWN et al., loc. cit. Several hundreds transformants were obtained by selecting for growth on tetracycline, the resistance to this antibiotic being conferred by the pBR322 plasmid. Transformants were also assayed for sensitivity to ampicillin. Those which are sensitive contain a chimeric plasmid since insertion of foreign DNA in the vector inactivates the ampicillin gene.

Screening of the cDNA library

*E. coli* transformants were screened with $^{32}P$ 5' end-labelled synthetic oligonucleotides corresponding to a fragment of the apo A-I gene. The nucleotide sequence of human apo A-I is known (see P. CHEUNG et L. CHAN, loc. cit. and J. J. SEILHAMER et al., loc. cit.); it is therefore convenient to synthesize chemically by the method of N. D. SINHA et al., (Nucleic Acids Res. 12, (1984), 4539–4557), a 22-base-long oligonucleotide probe corresponding to the 5' end of the gene. The selected sequence is as follows: 5'-GCTGCGGTGCTGACCTTGGCCG-3'. The synthetic oligonucleotide was phosphorylated at its 5' end using T4 polynucleotide kinase (P-L Biochemicals) and [gamma-$^{32}P$]ATP before being used for hybridization experiments. Conditions for labelling and for hybridization are well-known in the art and described in details by T. MANIATIS et al., loc. cit. and by A. BOLLEN et al., (DNA, 2, (1983), 255–264).

Construction of the expression plasmids

The procedures for DNA preparation, DNA fragment isolation, as well as the conditions for restriction enzymes analysis and for ligations of fragments are well-known in the art and described in details by R. M. LAWN et al., loc. cit. and by T. CABEZON et al., loc. cit. and are applicable herein. Synthesis of fragments connecting the promoter of expression vectors and 5' end of the gene are described hereinafter.

Synthesis of NcoI-BalI fragment

The principles underlying the design of the 35-mer, 30-mer, 18-mer and 43-mer oligonucleotides used to synthesize the 65/61 bp NcoI-BalI fragment are presented in detail in FIG. 2. The 30-mer and the 18-mer synthetic fragments were phosphorylated at their 5' ends using T4 polynucleotide kinase (P-L Biochemicals). 1 µg of each oligonucleotide, including the non-phosphorylated 35-mer and 43-mer, were annealed together for 3 minutes at 95° C. in 300 mM sodium acetate (pH 7.0) and allowed to cool slowly to 4° C. The annealing reaction was used as such in the cloning procedure for the construction of the expression plasmids.

DNA sequencing

DNA sequence analysis was performed by the methods of A. M. MAXAM and W. GILBERT (Proc. Natl. Acad. Sci. USA, 74, (1977), 560–564) and F. SANGER et al., (Proc. Natl. Acad. Sci. USA, 74, (1977), 5463–5467).

Protein analysis

Cell pellets containing 1 $OD_{630}$ unit were obtained at various stages during the fermentation of strains carrying the human proapo A-I expression plasmids pULB9291, pULB9292, pULB9296 and pULB9299 (transformed into E. coli strain AR58, JM101 or into yeast strain 10S44c, respectively). Each sample was resuspended in 50 mM Tris-HCl buffer, pH 6.8, containing 2% sodium dodecyl sulfate (SDS), 6M urea, 10% glycerol and 5% 2-mercaptoethanol, and boiled for 3 minutes. Samples were subjected to electrophoresis in polyacrylamide gels of U. K. LAEMMLI, (Nature, 227, (1970), 680–685). Total protein was visualized by Coomassie Brilliant Blue staining and synthesized human proapo A-I was identified by Western blot analysis (see A. BOLLEN et al., loc. cit.).

Construction of recombinant vectors for the expression of human proapo A-I in bacteria, yeast and baculovirus infected insect cells 1. Initial cDNA clone for human preproapo A-I: pULB1609 (FIG. 1).

Several hundred transformants, derived from the cloning, into the PstI site of pBR322, of cDNAds corresponding to human liver polyA+ RNA, were screened with the 22-mer apo A-I synthetic probe described above. One of the clones gave a strong hybridization signal in the assay. This clone, designated pULB1609, was recovered and the DNA insert present in the recombinant plasmid was characterized by DNA sequence analysis. Its length is 878 base pairs (bp); it encodes the full-length preproapo A-I polypeptide. As shown in FIG. 1, the cloned cDNA fragment carries 5' and 3' non-coding regions (19 bp and 55 bp, respectively), the 54 bp sequence coding for the precursor peptide (aa-24 to aa-7), the 18 bp sequence coding for the propeptide (aa-6 to aa-1) and the 732 bp sequence coding for mature apo A-I (aa1 to aa 243) and including the translational stop codon. The protein sequence deduced from the DNA sequence fits perfectly well with the amino acid sequence obtained from the protein and from independently isolated cDNA clones for preproapo A-I (W. C. BARKER et al., Comp. Biochem. Physiol. 57B, (1977), 309–315; Japanese patent application No. 96998/86; P. CHEUNG and L. CHAN, loc. cit. and J. J. SEILHAMER et al., loc cit.).

2. Construction of a bacterial expression vector containing the human proapo-A-I cDNA sequence: pULB9291 (FIGS. 2 and 3).

pULB9291, a plasmid producing human proapo A-I, was constructed by placing a segment derived from clone pULB1609 behind the regulatable $P_L$ lambda promoter (FIG. 3). The construction of this expression plasmid required the synthesis of DNA fragments comprising a NcoI cleavage site, an ATG translation initiation codon and the nucleotide sequence encoding the amino acids at the amino terminus of the human proapo A-I structural gene, up to the first unique restriction site, BalI (FIG. 2).

This adapter was synthesized by chemical procedures (N. D. SINHA et al., loc. cit.). Four synthetic oligonucleotides were synthesized; when annealed, they encode methionine corresponding to the ATG translation initiation codon, the 6 amino acids corresponding to the propeptide and the first 14 amino acids of mature human apo A-I (FIG. 2). The synthetic adapter was designed to minimize secondary structures in the 5' end of the gene. To do this, the codons selected to encode amino acid residues −6, −1, 1, 3, 4, 5, 6, 7, 10, 11 and 14 do not correspond to the natural codons observed in the pULB1609 cDNA clone.

The synthetic adapter, described above, was used to join a 744 bp DNA fragment derived from pULB1609 to the $P_L$ lambda promoter in the expression plasmid pULB1221.

The construction of expression vector pULB1221 is described in European patent application No. 186,643. It comprises three major steps starting from plasmid pCQV2. Plasmid pCQV2 has been described by C. QUEEN in J. Mol. Appl. Genet. 2, (1983), 1–10 and is freely available. The choice of this particular vector is not compulsory; any other vector having a promoter and an appropriate NcoI site downstream to it, can be used. Approximatively 0.1 μg of annealed synthetic fragments, as described above, were ligated with T4 DNA ligase to about 1 μg of the 744 bp BalI-PstI fragment derived from pULB1609 and about 1 μg of the vector pULB1221 cut with NcoI and BalI. Prior to the ligation, the 744 bp BalI-PstI fragment was treated with T4 DNA polymerase to flush 3' protruding ends; the procedure is well-known in the art and is described in details in T. MANIATIS et al., loc. cit.

Reconstructed plasmids, once amplified in E. coli AR58 competent cells, were characterized by restriction site analysis and DNA sequence of the synthetic portions and of the junction sites. One recombinant plasmid, pULB9291, satisfied all criteria since it had the fragments in the correct order and orientation and was used for expression studies.

3. Construction of a bacterial expression vector containing the fused sequences corresponding to beta-galactosidase and human proapo A-I: pULB9296 (FIG. 4).

In this construction, the DNA sequence coding for human proapo A-I was fused, downstream and in the correct reading frame, to the DNA sequence of beta-galactosidase. The gene for beta-galactosidase is present on an E. coli expression plasmid, freely available, pUR288 (U. RUTHER and B. MULLER-HILL, EMBO J. 2, (1983), 1791–1794) which carries an efficiently inducible lac promoter and appropriate restriction sites into the beta-galactosidase sequence. The appropriate recombinant plasmid was constructed as shown in FIG. 4. First, pUR288 plasmid DNA was successively cut with BamHI, treated with T4 DNA polymerase and cut again with SalI. Secondly, a 805 bp DNA fragment was derived from pULB9291 by successively digesting with KpnI, treating with T4 DNA polymerase and then digesting with SalI. The two fragments were ligated together, in molar ratios, with T4 DNA ligase and the resulting plasmid was used to transform E. coli competent cells, strain JM101, a widely and freely available strain (ATCC No. 33876). Transformants were checked by restriction analysis for the correct orientation of the human proapo A-I sequence with respect to the beta-galactosidase gene and for the presence of a reconstituted BamHI site at the junction of the two sequences. This indicated that the human proapo A-I sequence was fused downstream to the beta-galactosidase DNA sequence and in the correct reading frame. One of the transformants, pULB9296, satisfied all criteria and was used for expression experiments.

4. Construction of a yeast expression plasmid carrying the human proapo A-I cDNA sequence: pULB9299 (FIG. 5).

In this construction, the cDNA sequence coding for human proapo A-I was cloned between the promoter and terminator signals carried by a yeast expression plasmid. The yeast expression vector pRIT 10774 was selected for the experiment. The construction of expression plasmid pRIT 10774 is described in European patent application No. 151,102. It was constructed starting, on the one hand, from plasmid pRIT 10749, which has been deposited under the terms of the Budapest Treaty in the ATCC under accession number 39133 and, on the other hand, from E. coli-S. cerevisiae shuttle vector YEp13, described by J. R. BROACH et al., in Gene, 8, (1979), 121-133 which is available from the ATCC under accession number 37115. Vector pRIT 10774 can replicate in both E. coli and yeast and carries the ornithine carbamoyl transferase (ARG3) promoter and transcription terminator separated by a unique BamHI restriction site convenient for the insertion of a foreign DNA having its own ATG translation initiation codon. In addition, the vector carries yeast 2μ sequences, metabolic markers for selection in yeast and the AmpA selection marker for shuttling in E. coli. It is not the only vector which can be used for the expression of human proapo A-I in yeasts: any other yeast vector carrying regulatory signals could be used and would lead to qualitatively similar results. The construction depicted in FIG. 5 proceeded as follows. pRIT 10774 plasmid DNA was linearized with the enzyme BamHI and treated with T4 DNA polymerase.

On the other hand, a 810 bp DNA fragment was derived from pULB9291 by digestion with the enzymes Asp718 and SalI, followed by treatment with T4 DNA polymerase. This fragment encodes human proapo A-I polymerase. This fragment encodes human proapo A-I and includes the ATG translation initiation codon. The two fragments, obtained as described above, were ligated together in equimolar ratios with T4 DNA ligase and the mixture was used to transform E. coli MM294 competent cells. Transformants were checked by restriction analysis to verify the correct orientation of the proapo A-I DNA sequence with respect to the ARG3 promoter sequence. One of the transformants carried a recombinant plasmid, pULB9299, satisfying this condition. The plasmid pULB9299 was amplified in E. coli and used to transform spheroplasts of the yeast Saccharomyces cerevisiae strain 10S44c (pep4-3, leu2-3, leu2-112); (T. CABEZON et al., loc. cit.). The use of strain Ic 1679d (ATCC No. 20631) would lead to qualitatively similar results. Yeast transformants were then assayed for expression of human proapo A-I.

5. Construction of a bacterial secretion vector containing the human proapo A-I cDNA sequence: pNIV1612 (FIGS. 6A, B and C).

In this construction, the DNA sequence coding for human proapo A-I was fused, downstream and in the correct reading frame, to the DNA sequence of the E. coli Ompa protein signal peptide. The secretion vector pIN-III-ompA-2 (J. GHRAYEB et al., EMBO J. 3, (1984), 2437-2442) was selected for this experiment. This vector and its host strain E. coli JA221 are available on request from the Department of Biochemistry of the State University of New York at Stony Brook.

The secretion vector carries a strong lpp (lipoprotein) promoter, a lac promoter-operator fragment, the lacI sequence of the lac repressor and appropriate restriction sites immediately after the sequence coding for the ompA signal peptide. The appropriate recombinant plasmid was constructed as shown in FIGS. 6A, B, C. First, the secretion vector pIN-III-ompA-2 was linearized with EcoRI and treated with T4 DNA polymerase. Secondly, a 805 bp DNA fragment was derived from pULB9291 by successively digesting with the restriction enzymes KpnI and SalI, followed by treatment with T4 DNA polymerase. This fragment encodes human proapo A-I and includes the ATG translation initiation codon. The two fragments obtained, as described above, were ligated together in equimolar ratios with T4 DNA ligase and the mixture was used to transform E. coli JA221 competent cells grown in M9 medium (J. H. MILLER, in "Experiments in Molecular Genetics", Cold Spring Harbor Laboratory, Cold Spring Harbor, N.Y., 1972, p. 431) containing tryptophane (20 mg/l), leucine (20 mg/l), lactose (2 g/l) and ampicillin (50 mg/l).

Transformants were selected for their ampicillin resistance and screened with a 18-mer synthetic oligonucleotide (the same as used in the synthesis of the adapter, as shown in FIG. 2). The selected transformants were checked by restriction analysis to verify the correct orientation of the proapo A-I DNA sequence with respect to the signal peptide sequence carried by the secretion vector (reconstituted EcoRI site at the junction of the two sequences). One of the transformants carried a recombinant plasmid satisfying this condition. The extra sequence due to the linker after construction, underlined in the following nucleotide sequence 5' GTA GCG GAG GCC <u>GCT GAA TTC ATG</u>
   Val  Ala  Gln  Ala  Ala  Glu  Phe  Met AGA CAT TTC TGG 3'
Arg  His  Phe  Trp
aa-6 was removed by oligonucleotide-directed site-specific mutagenesis. For this purpose, the 24-mer oligonucleotide signal peptide  ⟶  ⟵  proapo A-I
5' GTA GCG GAG GCC AGA CAT TTC TGG 3'
  Val  Ala  Gln  Ala  Arg  His  Phe  Trp lacking the twelve excedentary bases, was synthesized and used to remove the 12-base linker sequence.

For the mutagenesis, the Amersham system is used. This system is based on the method of F. ECKSTEIN et al. (Nucleic Acids Res. 13, (1985), 8765-8785). The method gives a high yield of plaques and the highest available efficiency: up to 95%. First, the region of the DNA to be mutagenized is cloned in an M13 vector. For this, the XbaI-BalI DNA fragment of the recombinant plasmid pIN-III-ompA-2 carrying the proapo A-I gene is inserted in the M13mp19 vector cut by XbaI and HindII. Vector M13mp19 is commercially available; it can be obtained from Amersham (Buckinghamshire, England). Then, the mutagenic 24-mer oligonucleotide is annealed to the single-stranded template and extended by the Klenow fragment of DNA polymerase in the presence of T4 DNA ligase to generate a mutant heteroduplex.

Selective removal of the non-mutant strand is made possible by the incorporation of a thionucleotide into the mutant strand during the in vitro synthesis, and nicking by NCiI of the non-phosphorothionate strand. Such nicks present sites for exonuclease III, which digests the non-mutant strand. The mutant strand is then used as a template to reconstruct the double-stranded circular molecule, creating a homoduplex mutant molecule.

The mutagenesis was checked by sequencing the junction of the signal peptide and the beginning of the proapo A-I gene. The recombinant plasmid, pNIV1612, was reconstructed by ligating the XbaI-HindIII fragment of the pIN-III-ompA-2 vector with the XbaI-BalI DNA fragment from which the 12 excedentary bases have been deleted and with the BalI-HindIII fragment of the proapo A-I gene. The three fragments were ligated with T4 DNA ligase and the mixture was used to transform E. coli JA221 competent cells as described above. Transformants were selected for their ampicillin resistance and screened with the above-mentioned 18-mer oligonucleotide. One of the transformants carried a recombinant plasmid pNIV1612. In the final construct, the sequence coding for the ompA signal peptide precedes the complete proapo A-I sequence without the ATG codon (FIGS. 6A, B and C). E. coli transformants were then assayed for expression of human proapo A-I.

6. Construction of a transfer vector for the introduction of human proapo A-I cDNA sequence into baculovirus: pNIV1613 (FIG. 7).

pNIV1613, a plasmid carrying human proapo A-I DNA sequence was constructed by placing a segment derived from clone pULB9291 downstream to the polyhedrin gene promoter of the baculovirus (FIG. 7). The Baculovirus transfer vector pAcRP6 (Y. MATSU-URA et al., J. Gen. Virol., 67, (1986), 1515-1529), was used in the experiments; it can be obtained from the Department of Microbiology and Immunology of the University of Ottawa. The plasmid carries the polyhedrin gene promoter up to nucleotide −7 in the 5′ leader sequence; it lacks the polyhedrin ATG codon and the first 170 nucleotides of the polyhedrin coding sequence. A convenient BamHI site is located downstream to nucleotide −7. The construction depicted in FIG. 7 proceeded as follows. pAcRP6 plasmid DNA was linearized with BamHI. On the other hand, a 810 bp DNA fragment was derived from pULB9291 by digesting with the restriction enzymes Asp718 and SalI. This fragment encodes human proapo A-I and includes the ATG translation initiation codon. The two fragments, in equimolar ratios, were treated together with T4 DNA polymerase, ligated with T4 DNA ligase and used to transform E. coli AR58 competent cells. Transformants were selected for their ampicillin resistance, screened with a $^{32}$P- labelled synthetic 35-mer oligonucleotide (see FIG. 2) corresponding to part of the proapo A-I DNA sequence and checked by restriction analysis to verify the correct orientation of the proapo A-I DNA sequence with respect to the polyhedrin gene promoter. One of the transformants carried a recombinant plasmid, pNIV1613 satisfying this condition, and was used for expression experiments.

7. Production of human proapo A-I by transformed microorganisms.

20 ml cultures of E. coli strain AR58 or JM101, transformed with pULB9291 and pULB9296 respectively, were grown in rich medium supplemented with 50 μg/ml ampicillin (LB broth, see T. MANIATIS et al., loc. cit., for experimental details) until the optical density at 630 nm ($OD_{630}$) reached 0.6. In the case of pULB9291, induction of the $P_L$ lambda promoter was achieved by shifting the culture from its initial growth conditions (30° C.), to 42° C. in order to inactivate the repressor of the $P_L$ lambda promoter (M. ROSENBERG et al., Methods Enzymol. 101, (1983), 123–138). Induction was performed for 20 minutes.

In the case of pULB9296, induction of the lac promoter was achieved by adding to the culture, growing at 37° C., the chemical inducer IPTG (isopropyl-beta-D-thiogalactoside) to a final concentration of 1 mM (L. LORENZETTI et al., loc. cit.). Induction was performed for 60 minutes. On the other hand, 20 ml cultures of yeast cells 10S44c, transformed with pULB9299, were grown at 30° C. in yeast nitrogen base medium (Difco) supplemented with glucose (1%) up to an $OD_{630}$ of 0.3. No inducer was needed since the expression is constitutive in this particular case. One ml aliquots of the above cultures were collected and centrifuged at 15,000 g for 5 minutes. The obtained pellets were lysed in boiling sodium dodecyl sulfate (SDS) as follows. The pellets were resuspended in 50 μl of SDS sample buffer (50 mM Tris-HCl, pH 6.8, 2% SDS, 6M urea, 5% 2-mercaptoethanol and 10% glycerol) and boiled for 3 minutes at 100° C. Extracts were then centrifuged for 10 minutes at 15,000 g. The samples are then ready to perform the electrophoretic analysis on 15% or 7.5% SDS-polyacrylamide slab gels in denaturing conditions (U.K. LAEMMLI, loc. cit.).

After electrophoresis, the polyacrylamide slab gels were washed briefly with 40 ml distilled water and with 40 ml 50 mM sodium phosphate buffer at pH 7.5. Transfer of the proteins from the gels onto nitrocellulose sheets was then performed electrically for two hours at 60 V and 1.5 A in the same phosphate buffer (T. CABEZON et al., loc. cit.). The nitrocellulose sheets were saturated with albumin (1%) in 50 mM sodium phosphate buffer at pH 7.5, then incubated overnight at room temperature in the presence of a 1/500 dilution of rabbit anti-human apo A-I serum (and of mouse anti-beta-galactosidase monoclonal antibodies in the case of pULB9296) in the same buffer but without albumin.

The sheets were washed 5 times with 40 ml of the same phosphate buffer and then incubated with peroxydase-labelled goat anti-rabbit (or anti-mouse) serum (10 μg/ml) in 40 ml phosphate buffer. After 4 hours of incubation at room temperature, the sheets were washed again 5 times in 40 ml phosphate buffer and finally revealed by adding 50 ml of a chromogenic substrate solution (10 mg diaminobenzidine, 100 μl urea peroxide (10%), 100 mM Tris-HCl at pH 7.6). A single product reacting with the anti-human apo A-I antibodies was found in the case of pULB9291 and pULB9299. It has a molecular weight consistent with the one of standard natural apo A-I. In the case of pULB9296, a fused polypeptide reacting with anti-human apo A-I serum and with anti-beta-galactosidase serum was found at the expected size for the sum of the beta-galactosidase and proapo A-I polypeptides (144 kDa). Sizes were determined from a calibration curve based on the migration of molecular weight standards run on the same gel as the cell extracts.

In an other experiment, 20 ml cultures of E. coli strain JA221, transformed with pNIV1612 were grown in rich medium supplemented with 50 μg/ml of ampicillin (LB broth, see T. MANIATIS et al., loc. cit.) until the optical density at 630 nm reaches 0.6. Induction of the lac promoter was achieved by adding to the culture, growing at 37° C., the chemical inducer IPTG (isopropylbeta-D-thiogalactoside) to a final concentration of 2 mM. Induction was performed for 60 minutes. One ml aliquots of the cultures was collected and centrifuged at 15,000 g for 5 minutes. The obtained pellets were submitted to a mild osmotic shock in order to release the periplasmic fraction (D. KOSHLAND and D. BOTSTEIN, Cell, 20, (1980), 749–760). The released fraction was resuspended in the above-mentioned SDS sample buffer, without urea, boiled, centrifuged and submitted to a 12.5% SDS-polyacrylamide gel electrophoresis, followed by a Western blot analysis. A fraction of the synthesized965 proapo A-I is found in the cell and not in the periplasm. This is due either to the fact that some proapo A-I is not secreted, or that the efficiency of the osmotic shock is not optimal. The main fraction of proapo A-I was found to be released into the medium after the osmotic shock, indicating that the protein was secreted by the cells.

8. Production of human proapo A-I by baculovirus infected insect cells.

The recombinant plasmid pNIV1613 has been used in conjunction with the wild type baculovirus to coinfect *Spodoptora frugiperda* cells in culture. Screening for polyhedrin defective recombinant viruses gave recombinant plaques. The recombinant virus, purified from a plaque was used to infect insect cells. The procedure is well-known in the art and is described in details by M. D. SUMMERS and G. E. SMITH in "A Manual of Methods for Baculovirus Vectors and Insect cell culture Procedures, Texas University, College Station, (1987)". The recombinant virus was assayed for the production of proapo A-I by Western blot analysis and by electrophoresis on a 12.5% SDS-polyacrylamide gel after lysis of the cells with the RIPA buffer (0.05M Tris-HCl buffer, pH 7.2, containing 0.15M NaCl, 1% Triton X100, 0.1% SDS, 0.1% sodium deoxycholate and 1 mM phenylmethylsulfonyl fluoride (PMSF)) and treatment with boiling sodium dodecyl sulfate. A single product reacting with the anti-human apo A-I antibodies was found. It has a molecular weight consistent with the one of standard natural apo A-I and the expressed protein represents a major component of the total proteins content. The concentration of proapo A-I measured by single radial immunodiffusion (G.MANCINI et al., Immunochem. 2, (1965), 235–254) was estimated to be about 100 mg of proapo A-I per culture liter.

9. Cytoplasmic production of human proapo A-I in *E. coli*. Use of a defined minimal medium.

For the cytoplasmic production of human proapo A-I in *E. coli* in minimal medium, the plasmid pULB9292 was used. pULB9292 was constructed by exchanging the fragment EcoRI-NcoI of the plasmid pULB 9291, coding for the $P_L$ lambda promoter, for the same fragment EcoRI-NcoI of the plasmid pOTS. (M. ROSENBERG et al., Methods Enzymol. 101, (1983), 123–138). The fragment EcoRI-NcoI of the pOTS vector (G. DEVARE et al., Cell, 36, (1984), 43–49) contains also the efficient regulatable $P_L$ promoter of phage lambda. 20 ml cultures of *E. coli* strain AR58 transformed with pULB9292 were grown in a defined minimal medium. The composition of the minimal medium is (per liter): 3 g $Na_2HPO_4.2H_2O$; 3 g $KH_2PO_4$; 0.5 g NaCl; 1 g $NH_4Cl$; 1.37 mM $MgSO_4.7H_2O$; 29.5 $\mu M$ $FeCl_3.6H_2O$; 236 $\mu M$ $MnSO_4.H_2O$; 10 g glucose; 1 mg vitamin B1, 50 mg ampicillin; LB broth 1/20 (v/v). Cells were grown in this minimal medium to an $OD_{630}$ of 0.5. Induction of the $P_L$ lambda promoter was achieved by shifting the initial growth conditions of the culture from 30° C. to 42° C. in order to inactivate the repressor of the $P_L$ lambda promoter (M. ROSENBERG et al., loc. cit.). Induction was performed for 60 minutes. One ml aliquots of the cultures were collected and passed through the French's press or centrifuged at 15,000 g for 5 minutes. The obtained total cell extract or the pellet were treated with boiling SDS as described in § 7.

After electrophoresis and Western blot analysis, a single product reacting with the anti-human apo A-I antibodies was found. It has a molecular weight consistent with the one of standard natural apo A-I. The amount of expressed proapolipoprotein A-I in the defined minimal medium represents 13.5% of the total proteins content, i.e. an estimated concentration of proapo A-I of about 270 mg per culture liter.

10. Isolation, purification and characterization of human proapo A-I produced by transformed microorganisms.

10.1. Isolation and purification.

Crude extracts of the recombinant proapo A-I were centrifuged for 15 minutes at 4,000 g and the pellet was discarded. The supernatant was centrifuged at 100,000 g for two hours. The resulting pellet was resuspended in a minimal volume of a buffer (TEN100) consisting of 20 mM Tris-HCl, pH 7.5; 1 mM EDTA; 100 mM NaCl; 1.75 $\mu$g/ml PMSF and 100 $\mu$g/ml sodium merthiolate ([(o-carboxyphenyl)thio]ethylmercury sodium salt) and the volumes of this suspension and of the supernatant were adjusted separately to the original extract volume with the same buffer. Then, protein was precipitated from both suspensions using increasing isopropyl alcohol concentrations. The precipitated protein fraction of each suspension which contained the major part of the human apo A-I related immunoreactivity was determined by radial immunodiffusion (G. MANCINI et al., loc. cit.) using commercial apo A-I as standard. Each fraction thus obtained was further purified by chromatography through a column of Sephacryl S200, using the same buffer as eluent. Fractions of 0.9 ml were collected and the amounts of total protein having the immunoreactivity of apo A-I were determined in each fraction by radial immunodiffusion. The molecular weight of the eluted protein in the fractions was determined by calibrating the column with molecular weight standards such as aldolase, bovine serum albumin, ovalbumin, chymotrypsinogen and cytochrome C2, under identical conditions.

The purity of the proapo A-I per mg of total protein in the major recombinant proapo A-I containing fractions, expressed in mg of protein having the same immunoreactivity as a standard commercially prepared apo A-I, was estimated to be 95%.

10.2. Characterization.

10.2.1. Physical properties of recombinant proapo A-I. When subjected to isoelectric focusing, according to the procedure of N. CATSIMPOOLAS (Anal. Biochem. 26, (1969), 54–62), and applying a self generating gradient from pH 4 to pH 6, recombinant proapo A-I isolated and purified from the supernatant and from the pellet of the centrifugation at 100,000 g (10.1 above) show one single band, having an estimated isoelectric point of 4.95.

Human plasma apo A-I was shown to be slightly more acidic; it has an estimated isoelectric point of 4.75. This difference of 0.2 pH units between the isoelectric point values of recombinant proapo A-I and plasma apo A-I is in good agreement with the known difference in isoelectric point values between plasma apo A-I and plasma proapo A-I; this difference has been reported to be 0.17 (G. L. MILLS et al., Lab. Tech. Biochem. Mol. Biol. 14, (1984), 244–245). With respect to molecular weight, both pellet and supernatant recombinant proapo A-I consist of one single polypeptide chain having identical molecular weights which were found to be 29.9±1.4 kDa. Human plasma apo A-I was found to be slightly smaller, having a molecular weight of 29.3±1.3 kDa.

10.2.2. Peptide mapping of recombinant proapo A-I with BNPS-skatol.

Chemical cleavage with 3-bromo-3-methyl-2-[(2-nitrophenyl)thio]-3H-indole (BNPS-skatol) was performed according to the procedure of A. FONTANA (Methods Enzymol. 25, (1972), 419–423). 5–10 μg of purified protein preparations were dissolved in 100 μl of a 0.15% (v/v) solution of phenol in 50% (v/v) aqueous acetic acid. Then, 50 μl of a solution of 4.8 mg of BNPS-skatol per ml of glacial acetic acid were added, followed by an incubation at 25° C. for 72 hours.

Subsequently, 50 μl of 2-mercaptoethanol were added, followed by a second incubation at 37° C. for 5 hours. The samples were evaporated, redissolved in 100 μl of water and extracted three times with 200 μl of ethyl acetate. The organic phases were discarded and the aqueous phases were lyophilized and analyzed by SDS-polyacrylamide gel electrophoresis.

In case of chemical cleavage with BNPS-skatol, the number and size of apo A-I derived fragments can more or less be predicted, since under the experimental conditions used, BNPS-skatol selectively cleaves after tryptophane residues. Assuming a 100% efficiency at each cleavage site, the largest fragment to be expected is a C-terminal fragment of 15.4 kDa. The molecular weights of the remaining fragments range from 0.5 up to 5.3 kDa and are therefore too small to be detected.

In case of incomplete cleavage, the 15.4 kDa fragment will be "extended" in the direction of the N-terminus, yielding fragments of 20.7 kDa, 23.1 kDa and 27.6 kDa respectively. These expectations are nicely met for human plasma apo A-I as well as for the different purified preparations of recombinant proapo A-I.

We claim:

1. A recombinant DNA sequence coding for human proapolipoprotein A-I and capable of reducing the formation of hairpins, which comprises (a) a synthetic DNA fragment having the nucleotide sequence:

5'-ATGAGACATTTCTGGCAGCAGGAC-
GAACCTCCACAATCTCCTTG-
GGATAGAGTTAAGGACTTG-3', coding for the amino acids −6 to +14 of human proapolipoprotein A-I, and (b) downstream from the said synthetic DNA fragment, the natural DNA sequence coding for the amino acids +15 to +243 of human proapolipoprotein A-I.

2. A recombinant DNA sequence coding for human proapolipoprotein A-I, wherein part of the natural coding sequence has been replaced by a synthetic DNA fragment coding for the same amino acids but consisting of a different nucleotide sequence such as to reduce or prevent formation of hairpins, said recombinant DNA sequence having the nucleotide sequence:

—ATGAGACATTTCTGGCAGCAGGACGAACCTCCACAA
   R   H   F   W   Q   Q   D   E   P   P   Q

-continued

TCTCCTTGGGATAGAGTTAAGGACTTGGCCACTGTGT
S P W D R V K D L A T V
          10             +14

ACGTGGATGTGCTCAAAGACAGCGGCAGAGACTATG
Y V D V L K D S G R D Y
    20

TGTCCCAGTTTGAAGGCTCCGCCTTGGGAAAACAGCT
V S Q F E G S A L G K Q L
30                         40

AAACCTAAAGCTCCTTGACAACTGGGACAGCGTGACC
N L K L L D N W D S V T
               50

TCCACCTTCAGCAAGCTGCGCGAACAGCTCGGCCCTG
S T F S K L R E Q L G P
        60

TGACCCAGGAGTTCTGGGATAACCTGGAAAAGGAGAC
V T Q E F W D N L E K E T
   70

AGAGGGCCTGAGGCAGGAGATGAGCAAGGATCTGGA
E G L R Q E M S K D L E
80                   90

GGAGGTGAAGGCCAAGGTGCAGCCCTACCTGGACGA
E V K A K V Q P Y L D D
         100

CTTCCAGAAGAAGTGGCAGGAGGAGATGGAGCTCTA
F Q K K W Q E E M E L Y
    110

CCGCCAGAAGGTGGAGCCGCTGCGCGCAGAGCTCCA
R Q K V E T L R A E L Q
    120

AGAGGGCGCGCGCCAGAAGCTGCACGAGCTGCAAGA
E G A R Q K L H E L Q E
   130

GAAGGTGAGCCCACTGGGCGAGGAGATGCGCGACCG
K L S P L G E E M R D R
140                  150

CGCGCGCGCCCATGTGGACGCGCTGCGCACGCATCTG
A R A H V D A L R T H L
      160

GCCCCCTACAGCGACGAGCTGCGCCAGCGCTTGGCC
A P Y S D E L R Q R L A
    170

GCGCGCCTTGAGGCTCTCAAGGAGAACGGCGGCGCC
A R L E A L K E N G G A
    180

AGACTGGCCGAGTACCACGCCAAGGCCACCGAGCAT
R L A E Y H A K A T E H
    190

CTGAGCACGCTCAGCGAGAAGGCCAAGCCCGCGCTC
L S T L S E K A K ·P A L
200                 210

GAGGACCTCCGCCAAGGCCTGCTGCCCGTGCTGGAG
E D L R Q G L L P V L E
       220

AGCTTCAAGGTCAGCTTCCTGAGCGCTCTCGAGGAG
S F K V S F L S A L E E
    230

TACACTAAGAAGCTCAACACCCAGTGA.
Y T K K L N T Q
    240

3. An expression vector comprising a recombinant DNA sequence as claimed in claim 1 or 2 and a regulatory DNA sequence which regulates the expression of said recombinant DNA sequence.

4. An expression vector as claimed in claim 3, wherein the regulatory DNA sequence comprises the phage lambda $P_L$ promoter region.

5. An expression vector as claimed in claim 3, wherein the recombinant DNA sequence is fused downstream from the beta-galactosidase DNA sequence and wherein the regulatory DNA sequence comprises the lac promoter region.

6. An expression vector as claimed in claim 3, wherein the regulatory DNA sequence comprises the yeast ARG3 promoter and transcription terminator regions.

7. An expression vector as claimed in claim 3, wherein the recombinant DNA sequence lacking the ATG codon is fused downstream from the DNA sequence of the E. coli OmpA protein signal peptide and wherein the regulator DNA sequence comprises the lpp promoter, the lac promoter-operator and the lac I sequence of the lac repressor.

8. An expression vector as claimed in claim 3, wherein the regulator DNA sequence comprises the baculovirus polyhedrin gene promoter region.

9. A cell culture or microorganism transformed with an expression vector as claimed in claim 3.

10. A cell culture or microorganism transformed with an expression vector as claimed in claim 4.

11. A cell culture or microorganism transformed with an expression vector as claimed in claim 5.

12. A cell culture or microorganism transformed with an expression vector as claimed in claim 6.

13. A cell culture or microorganism transformed with an expression vector as claimed in claim 7.

14. A cell culture or microorganism transformed with an expression vector as claimed in claim 8.

15. A process for producing human proapolipoprotein A-I which comprises culturing under appropriate cultivation conditions, a transformed cell or microorganism as claimed in claim 9 and recovering the human proapolipoprotein A-I so produced.

* * * * *